United States Patent [19]

Wollenhaupt

[11] Patent Number: 4,909,245

[45] Date of Patent: Mar. 20, 1990

[54] COMPACT DISPOSABLE MOUTH-TO-MOUTH RESUSCITATION DEVICE

[76] Inventor: William H. Wollenhaupt, 4016 Maricarr Dr., Kettering, Ohio 45429

[21] Appl. No.: 364,648

[22] Filed: Jun. 9, 1989

[51] Int. Cl.$^4$ ............................................. A61M 16/00
[52] U.S. Cl. ........................... 128/203.11; 128/202.28; 128/202.29
[58] Field of Search ....................... 128/202.28, 202.29, 128/203.11

[56] References Cited

U.S. PATENT DOCUMENTS

| | | |
|---|---|---|
| 3,018,775 | 1/1962 | Wilson et al. .................. 128/203.11 |
| 3,626,936 | 12/1971 | Barker . |
| 4,050,457 | 9/1977 | Davidson . |
| 4,510,931 | 4/1985 | Henderson et al. . |
| 4,520,811 | 6/1985 | White et al. ..................... 128/203.11 |
| 4,711,237 | 12/1987 | Kaiser . |
| 4,819,627 | 4/1989 | Connors ......................... 128/203.11 |
| 4,819,628 | 4/1989 | Eisenberg et al. ............. 128/203.11 |

FOREIGN PATENT DOCUMENTS 2742213 3/1979 Fed. Rep. of Germany .

Primary Examiner—Edgar S. Burr
Assistant Examiner—Aaron J. Lewis
Attorney, Agent, or Firm—Robert W. Becker & Associates

[57] ABSTRACT

A compact, disposable mouth-to-mouth resuscitation device that comprises: a rigid yet flexible thin plastic valve body that is provided with at least one valve port, and a first thin flexible plastic sheet that is disposed on that side of the valve body that is adapted to face the mouth of the subject on which the device is to be used. This plastic sheet is provided with slits to form at least one first valve flap, the number of which correspond to the number of valve ports. The valve flaps are hinged to the plastic sheet and cover the valve ports when the device is not being used. A second thin flexible plastic sheet can be disposed on the other side of the valve body, with this plastic sheet also being provided with slits to form valve flaps, the number of which also correspond to the number of valve ports. A foam element having a central opening can be disposed on the first plastic sheet remote from the valve body.

12 Claims, 2 Drawing Sheets

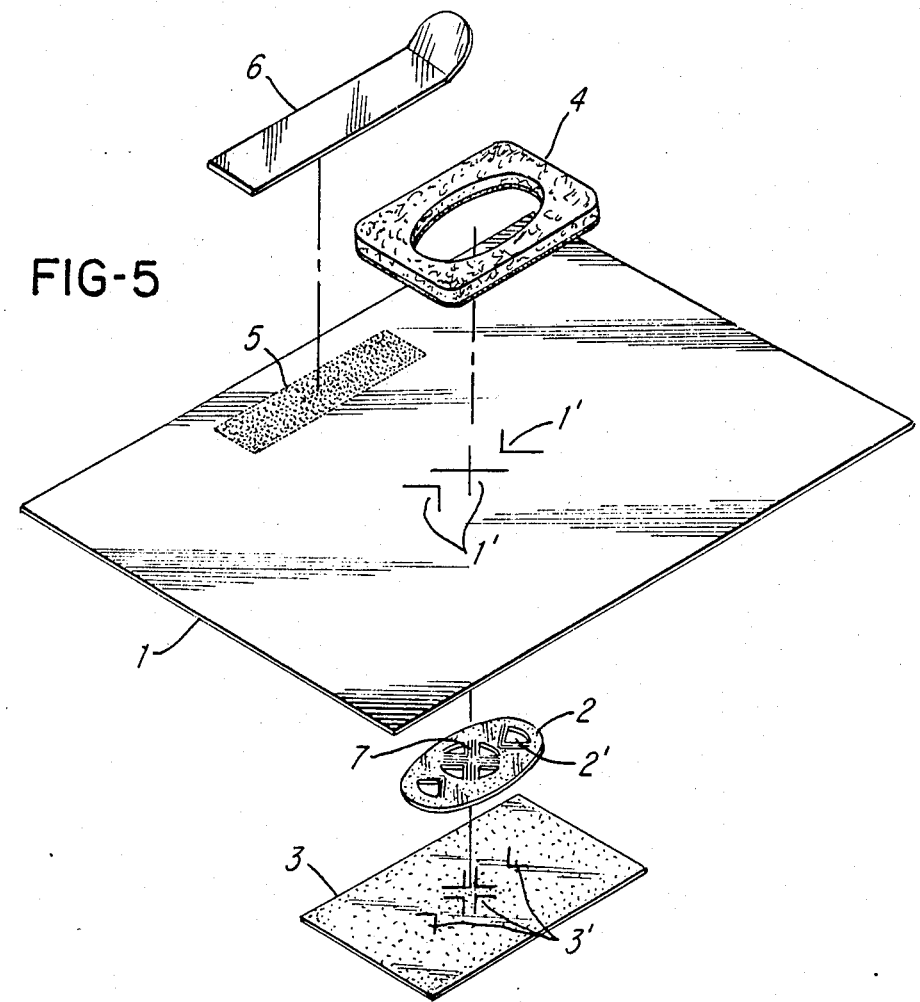
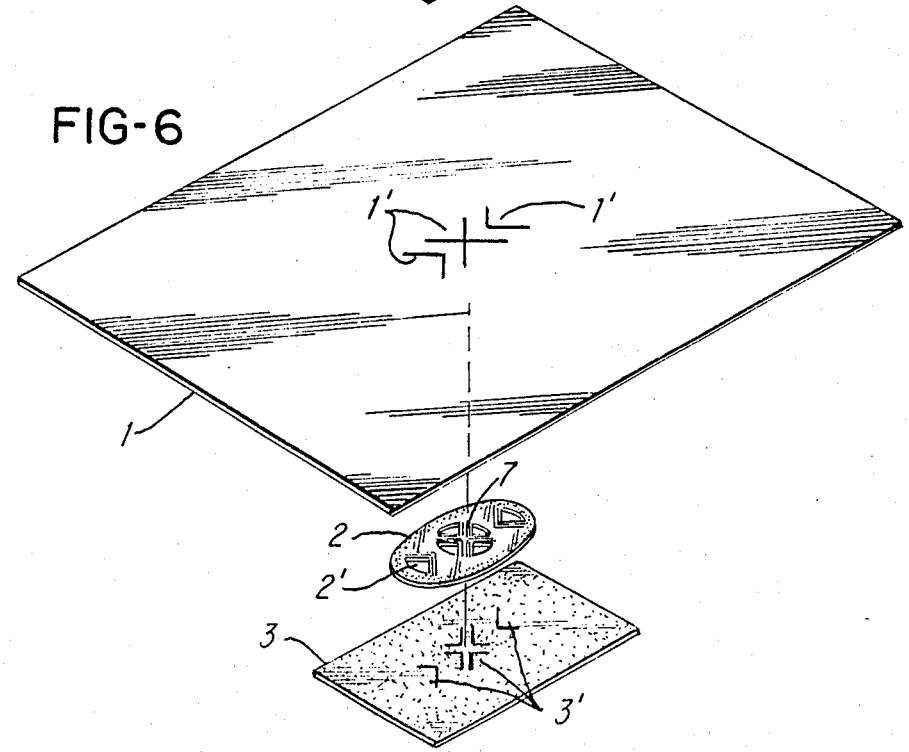

COMPACT DISPOSABLE MOUTH-TO-MOUTH RESUSCITATION DEVICE

BACKGROUND OF THE INVENTION

The present invention relates to a compact, throwaway, or disposable mouth-to-mouth resuscitation device.

Resuscitation devices are provided in order to be able to administer mouth-to-mouth resuscitation while at the same time avoiding direct lip contact with a patient. It is also desirable to be able to prevent a back flow to a rescuer from the mouth or nose of a person on whom the device is being used. Such devices are also very desirable for use in training classes, either with a live subject or with a CPR-type doll, especially for sanitary reasons.

Known resuscitation devices are not compact enough to be conveniently carried in a wallet, pocket, or purse, and/or are too expensive to be disposable. Examples of known devices include U.S. Pat. No. 4,711,237, Kaiser, Dec. 8, 1987, which is concerned with a different problem, inasmuch as it is provided for use on a CPR doll, and merely comprises a protective barrier sheet with a central opening but no one-way check-type valve; U.S. Pat. No. 4,510,931, Henderson et al, issued Apr. 16, 1985, which comprises a laminate of porous material, thus again not providing a one-way valve; U.S. Pat. No. 4,050,457, Davidson, issued Sept. 27, 1977, and comprising a sheet of thin flexible material that is provided with an unobstructed opening, i.e., is not provided with any type of check valve; U.S. Pat. No . 3 626,936 Daniel George John Barker, issued Dec. 14, 1971, including a valve device, the drawback of which is that it includes a substantially rigid valve plate and can therefore not fulfill the purposes outlined above; and German Offenlegungsschrift No. 27 42 213, published Mar. 22, 1979, which, as indicated in claim 1, comprises a centrally reinforced rectangular plastic sheet with a non-return valve, a muslin panel, and an oblong plastic bar to separate the tongue of the patient from the roof of the mouth. None of the aforementioned devices have proven to be satisfactory in fulfilling the aforementioned purposes.

It is therefore an object of the present invention to provide a compact, efficient mouth-to-mouth resuscitation device that is inexpensive enough to be disposable.

BRIEF DESCRIPTION OF THE DRAWINGS

This object, and other objects and advantages of the present invention, will appear more clearly from the following specification in conjunction with the accompanying schematic drawings, in which:

FIG. 5 is an exploded view of the device of FIG. 1; and

FIG. 6 is an exploded view of another, simplified exemplary embodiment of the inventive resuscitation device.

SUMMARY OF THE INVENTION

Figure 1:
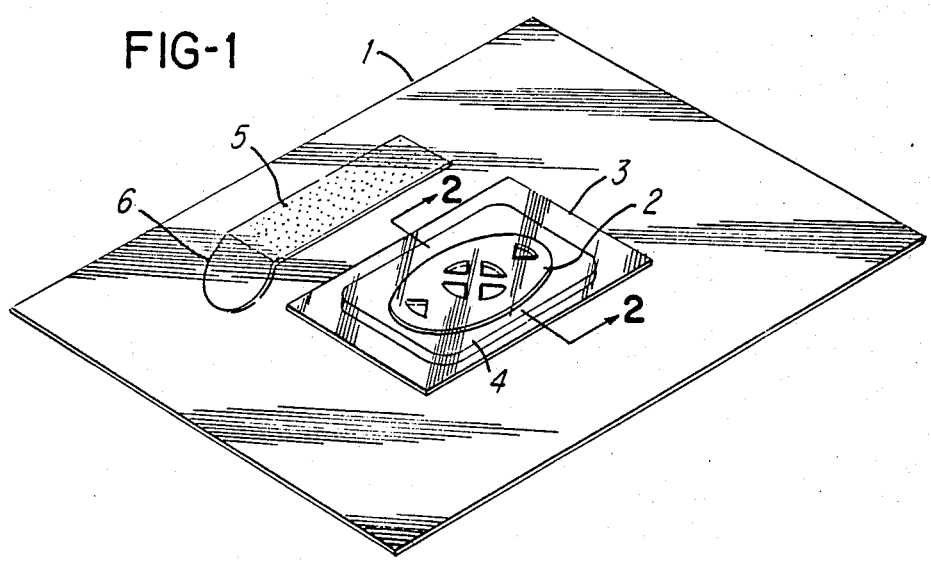
FIG. 1 shows one inventive embodiment of the inventive resuscitation device.

The mouth-to-mouth resuscitation device of the present invention is characterized primarily by: a rigid yet flexible thin plastic valve body that is provided with at least one valve port, with the valve body having a first side that is adapted to face the mouth of a CPR-type doll or person on whom the device is to be used, and a second side that is remote from the first side and a first thin flexible plastic sheet that is disposed on the first side of the valve body, with the plastic sheet being provided with slits to form at least one first valve flap, the number of valve flaps corresponding to the number of valve ports, with the valve flaps remaining hinged to the plastic sheet, and with the valve flaps covering the valve ports when the device is not being used, i.e. when a rescuer is not attempting to blow air through the resuscitation device and into the mouth of a CPR doll or person on whom the device is being used. This embodiment is the most straightforward version of the inventive mouth-to-mouth resuscitation device.

The resuscitation device of the present invention has several advantages. Due to its thin, compact nature when folded and packaged, it is essentially the size of a credit card and can easily be carried in a wallet, pocket, or purse. The valve flaps of the thin flexible plastic sheet, in conjunction with the thin plastic valve body and its valve ports, provide a one-way check valve arrangement so that when the inventive resuscitation device is placed over a patient's open mouth, the rescuer can blow through the device without having to fear back flow from the patient. Pursuant to one preferred embodiment of the inventive device, a second thin flexible plastic sheet is disposed on the second side of the valve body, with this second plastic sheet being provided with slits to form at least one second valve flap, the number of second valve flaps corresponding to the number of valve ports and hence to the number of first valve flaps, with the second valve flaps remaining hinged to the second plastic sheet, and with the second valve flaps being connected to the first valve flaps. The connection between the valve flaps of the first and second thin flexible plastic sheets can be effected in several ways. For example, one of the plastic sheets can be provided with adhesive, so that the flaps of the two plastic sheets adhere to one another. If the second plastic sheet is provided with an adhesive backing, this helps to also anchor the valve body to the first plastic sheet. Ridges could also be provided on one of the plastic sheets or on the valve body. In place of, as, or in combination with such ridges, which are intended to prevent capillary action, a slightly tacky silicone grease or rubber could be provided. This also helps the valve flaps of the first plastic sheet to "stick" to the valve body when the resuscitation device is not being used. It should be noted that the use of a second phasic sheet having valve flaps that are connected to the valve flaps of the first plastic sheet helps in pulling back the first valve flaps when a rescuer is not blowing through the device, thus enhancing the check valve characteristic of the inventive device.

It is also possible to provide a foam element on the first plastic sheet remote from the valve body, with this foam element being provided with either a single central opening or several openings to allow communication, via the valve flaps and the valve ports, between the mouth of the rescuer and the mouth of a person on whom the device is being used when the user blows through the device. Such a foam element has several purposes. For one thing, the foam element serves as a cushion between the device and the face of the person on whom the device is being used. The foam element also serves as an additional sealing element. Finally, the foam element helps a user to identify which side of the device is to be placed against the face of a person on whom the device is to be used; this is particularly useful in the dark.

Another feature that helps in properly positioning the inventive device on the mouth of a patient is the provision of a valve body that has an inherent arch to it. Although the device can still be flattened when placed, for example, in a wallet, it has a memory so that the device will again arch when it is removed from the wallet for use. It is to be understood that the first flexible sheet is disposed on the concave side of the valve body.

The plastic sheets and valve body are preferably clear in order to permit the patient to be observed.

An adhesive strip can be provided along the top edge of the first plastic sheet so that the inventive resuscitation device can be stuck to a patient's nose to help hold the device in position to allow, for example, the rescuer to perform other functions.

Although the number of valve ports and valve flaps are not critical, whereby even one port or flap in each of the components is enough to supply sufficient air to a patient, a greater number of holes gives a rescuer more flexibility in how the device is positioned over the mouth. In other words, it is not as necessary to be so precise, which can be particularly important in the dark. Thus, as indicated, the inventive resuscitation device can have one hole, two holes, or any other desired number of holes. Pursuant to one preferred embodiment, the inventive device is provided with four or six holes, with the term "hole" being used to describe the valve ports and valve flaps.

It should be noted that the inventive resuscitation device should preferably not be dispensed unless this is accompanied by training.

Further specific features of the present invention will be described in detail subsequently.

DESCRIPTION OF PREFERRED EMBODIMENTS

Referring now to the drawings in detail, the present invention will be described first in conjunction with the embodiment illustrated in FIGS. 1-5.

Figure 4:
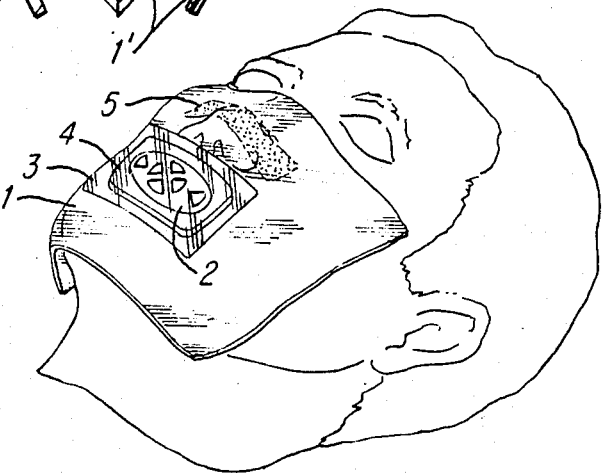
FIG. 4 shows the device of FIG. 1 in place on a CPR-type doll or person on whom the device is being used.

FIG. 1 shows an exemplary inventive resuscitation device from the side against which a user or rescuer would blow. FIG. 4 shows how the underside of the inventive resuscitation device has been placed against the face of a CPR doll or patient, with the novel one-way check valve structure having been placed over the open mouth of the subject.

Figure 2:
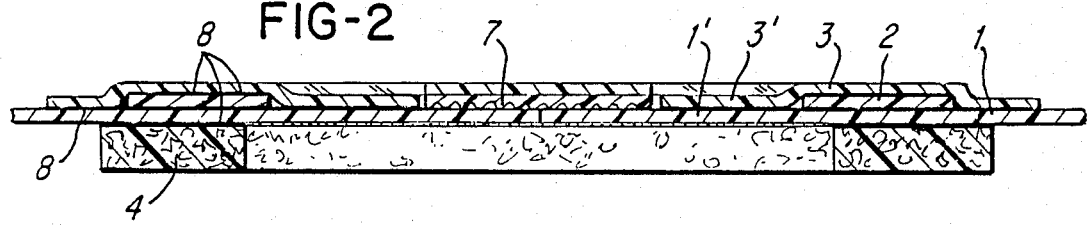
FIG. 2 is a cross-sectional view taken along the line 2—2 of FIG. 1, and shows the inventive device when not in use.
Figure 3:
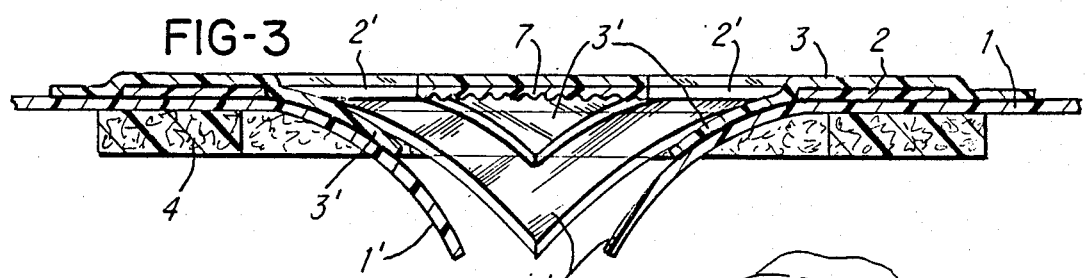
FIG. 3 is a view similar to FIG. 2 during use of the device and illustrates the one-way check valve characteristic of the valve flaps.

The various components of this exemplary embodiment of the inventive resuscitation device are shown particularly clearly in the cross-sectional views of FIGS. 2 and 3, and in the exploded view of FIG. 5. A thin flexible plastic sheet 1, for example of 1 or 2 mil thickness, is disposed over a rigid yet flexible thin plastic valve body 2 of, for example, 7-14 mil thickness, preferably about 10 mil. The valve body 2 is provided with one or more valve ports 2', which can be in the form of cutouts, holes, etc. of any convenient shape. Although six such holes or valve ports 2' are illustrated in the drawings, it would also be possible to have just a single, preferably centrally disposed, hole, or any other suitable number of holes, for example two, three, or four holes. The plastic sheet 1 is provided with slits to form the valve flaps 1', with the number of these valve flaps 1' corresponding to the number of valve ports 2' of the valve body 2. The valve flaps 1' are hinged to the plastic sheet 1 and cover the valve ports 2' when the device is not being used, i.e. when a user or rescuer is not blowing through the device in an attempt to resuscitate a patient. The valve flaps 1' are preferably larger than the valve ports 2' with which they are associated in order to more effectively cover the valve ports 2' when the device is not being used, or when a check valve action is required.

Provided on the opposite side of the valve body 2 is a further thin flexible plastic sheet 3, for example of 1-4 mil thickness. This plastic sheet 3 is similarly provided with slits to form valve flaps 3', the number of which again correspond to the number of valve ports 2' and hence to the number of valve flaps 1'. The valve flaps 3' are hinged to the plastic sheet 3, and are preferably connected to the valve flaps 1'. This connection helps to pull the flaps 1' back from an open position inasmuch as the connection puts tension on the valve flaps 3' when the same are open. The valve flaps 3' are preferably the same size as the valve ports 2' with which they are associated, and are adapted to extend through the valve ports when a user blows through the device (see FIG. 3).

The valve body 2 and the plastic sheets 1 and 3 may be made of a clear plastic in order to be able to view the patient.

Disposed on that side of the plastic sheet 1 remote from the valve body 2 is a foam element 4 of, for example, 0.030 to 0.125 inch thickness. In the illustrated embodiment, the foam element 4 is shown as having a single central opening 4'. However, several such openings could also be provided. The important thing is that the opening 4' permit communication from the side of the device facing a user to the mouth of a patient. In particular, when the user blows upon the device from the top side as seen in FIG. 3, the valve flaps 3' and 1' open toward the mouth of the patient, allowing air blown out by the user to pass through the valve flaps 3', the valve ports 2', the valve flaps 1', and the opening 4' into the open mouth of the patient. When the user stops blowing through the device, the valve flaps return to a closed position, whereupon the valve flaps 1' cover the valve ports 2', thus preventing any back flow, such as saliva or vomit, from passing through the device to the user. The foam element 4 serves not only as a cushion between the plastic sheet 1 and the face of the patient, but also serves as a sealing element about the mouth of the patient.

In the illustrated embodiment, the plastic sheet 1 is shown as being of such a size that those parts of the plastic that extend beyond the valve body 2 can be folded over to keep the rest of the device clean and to make the device compact enough to fit into a pocket or wallet. Note also, that although the illustrated embodiment shows the plastic sheet 1 as being large enough to cover not only the mouth but also the nose of a patient, for purposes of the present invention, the plastic sheet 1, as well as the entire device, need only be large enough to cover the mouth of a patient.

As shown in particular in FIGS. 1 and 5, the inventive device can also be provided with an adhesive strip 5. As shown in FIG. 4, when the device is being used the adhesive strip 5 helps to hold the device in place by sticking to the nose of a patient. Prior to use, this adhesive strip 5 is covered by a removable protective pull tab 6, which can be made, for example, of plastic. The pull tab 6 can be very easily removed to expose the adhesive strip 5.

It should be noted that the foam element 4 serves a further purpose. In particular, when the inventive resuscitation device is being used in the dark, a user can quickly identify by feel which side of the device is to be placed against the face of a patient. As a further means for identifying the proper orientation of the inventive device, especially where no foam element 4 is provided, it is possible to provide the valve body 2 with an inherent arch. Although the valve body 2 is flexible enough to be pressed flat, for example in a wallet, when the inventive device is removed for use, the inherent arch of the valve body 2 will give a curve to the entire device, whereupon a user can readily recognize that the concave side of the device should be placed against the face of a patient.

The various parts can be secured to one another in any suitable manner. For example, an adhesive 8 can be provided on one side of a pertaining part or can be placed between associated parts.

Since the valve flaps 1' must be able to move away from the valve body 2, these valve flaps can, of course, not be permanently secured to the valve body 2. However, in order to provide a more reliable closure of the valve flaps 1' against the valve body 2 for the purpose of closing off the valve ports 2', those portions of the valve body 2 against which the valve flaps 1' rest in a closed position can be provided with appropriate means to enhance the closure effect. For example, the valve body 2 can be provided with ridges 7. These ridges can either be inherently formed in the valve body or can be formed by silicone rubber or silicone grease that is provided on the valve body 2. This provides not only an easily releaseable adhesive means so that the valve flaps 1' can be released from the valve body 2 when a user blows through the device, but also provides an additional sealant means against back flow.

FIG. 6 illustrates one straightforward simplified exemplary embodiment of the inventive resuscitation device. In particular, the embodiment of FIG. 6 shows merely a valve body 2 with thin plastic sheets 1 and 3 on either side thereof. In an even more straightforward embodiment of the present invention, the plastic sheet 3 could be eliminated, so that the device would comprise merely a valve body 2 that is secured to a plastic sheet 1.

The present invention is, of course, in no way restricted to the specific disclosure of the specification and drawings, but also encompasses any modifications within the scope of the appended claims.

What I claim is:

1. A compact, disposable mouth-to-mouth resuscitation device, comprising:

a rigid yet flexible thin plastic valve body, said valve body having a flexible plastic sheet that is provided with at least one valve port, with said valve body having a first side that is adapted to face the mouth of a subject on which said device is to be used, and a second side remote from said first side; and a first thin flexible plastic sheet that is disposed on said first side of said valve body, with said first plastic sheet being provided with slits to form at least one first valve flap, the number of first valve flaps corresponding to the number of valve ports, with said valve flaps remaining hinged to said first plastic sheet, and with said first valve flaps covering said valve ports when said device is not being used; and a second thin flexible plastic sheet that is disposed on said second side of said valve body, with said second plastic sheet being provided with slits to form at least one second valve flap, the number of second valve flaps corresponding to the number of valve ports and hence to the number of first valve flaps, with said second valve flaps remaining hinged to said second plastic sheet, and with said second valve flaps being connected to said first valve flaps and in which each of said first valve flaps is larger than said valve port with which it is associated, and each of said second valve flaps is approximately the same size as said valve port with which it is associated.

2. A resuscitation device according to claim 1, which includes a foam element disposed on said first plastic sheet remote from said valve body, with said foam element being provided with central opening means to allow communication, via said second valve flaps, said valve ports, and said first valve flaps, to the mouth of a subject on which said device is being used when a user blows through said device.

3. A resuscitation device according to claim 2, in which said valve body includes four valve ports.

4. A resuscitation device according to claim 2, in which said valve body includes six valve ports.

5. A resuscitation device according to claim 2, in which said second plastic sheet is provided with an adhesive to enhance connection of said second valve flaps to said first valve flaps.

6. A resuscitation device according to claim 2, in which said valve body is provided with ridges to enhance said covering of said valve ports by said first valve flaps when said device is not being used.

7. A resuscitation device according to claim 6, in which said ridges are integral with said valve body.

8. A resuscitation device according to claim 6, in which said ridges are made of a material selected from the group consisting of silicone rubber and silicone grease.

9. A resuscitation device according to claim 2, in which said valve body is provided with an inherent arch.

10. A resuscitation device according to claim 2, in which said valve body and said first and second plastic sheets are made of clear plastic.

11. A resuscitation device according to claim 2, in which said first plastic sheet is provided with an adhesive strip on that side thereof remote from said valve body.

12. A resuscitation device according to claim 11, which includes a removable protective tab disposed on said adhesive strip.

* * * * *